(12) United States Patent
Le Prado et al.

(10) Patent No.: US 12,429,531 B2
(45) Date of Patent: Sep. 30, 2025

(54) VECTOR MAGNETOMETERS NETWORK AND ASSOCIATED POSITIONING METHOD

(71) Applicant: Commissariat A L'Energie Atomique et aux Energies Alternatives, Paris (FR)

(72) Inventors: Matthieu Le Prado, Saint-Marcellin (FR); Saifeddine Aloui, Fontaine (FR); Etienne Labyt, Saint-Martin-le-Vinoux (FR)

(73) Assignee: Commissariat A L'Energie Atomique et aux Energies Alternatives, Paris (FR)

( * ) Notice: Subject to any disclaimer, the term of this patent is extended or adjusted under 35 U.S.C. 154(b) by 1395 days.

(21) Appl. No.: 15/857,678

(22) Filed: Dec. 29, 2017

(65) Prior Publication Data

US 2018/0188334 A1     Jul. 5, 2018

(30) Foreign Application Priority Data

Jan. 2, 2017   (FR) ...................... 17 50010

(51) Int. Cl.
| | |
|---|---|
| A61B 5/06 | (2006.01) |
| A61B 5/00 | (2006.01) |
| A61B 5/243 | (2021.01) |
| A61B 5/245 | (2021.01) |
| G01R 33/00 | (2006.01) |
| G01V 3/08 | (2006.01) |

(52) U.S. Cl.
CPC .......... G01R 33/0005 (2013.01); A61B 5/062 (2013.01); A61B 5/243 (2021.01);
(Continued)

(58) Field of Classification Search
None
See application file for complete search history.

(56) References Cited

U.S. PATENT DOCUMENTS

| | | | | |
|---|---|---|---|---|
| 4,742,356 A | * | 5/1988 | Kuipers | F41G 3/225 342/386 |
| 5,913,820 A | * | 6/1999 | Bladen | A61B 34/20 600/407 |

(Continued)

FOREIGN PATENT DOCUMENTS

| | | | | |
|---|---|---|---|---|
| EP | 1 272 862 B1 | | 1/2005 | |
| EP | 2998758 A2 | * | 3/2016 | ............. A61B 5/245 |
| FR | 3026193 A1 | * | 3/2016 | ............. A61B 5/245 |

OTHER PUBLICATIONS

U.S. Appl. No. 14/856,950, filed Sep. 17, 2015, 2016/0084925 A1, Matthieu Le Prado, et al.*

(Continued)

*Primary Examiner* — Pascal M Bui Pho
*Assistant Examiner* — Michael S Kellogg
(74) *Attorney, Agent, or Firm* — Oblon, McClelland, Maier & Neustadt, L.L.P.

(57) ABSTRACT

The invention relates to a method of localisation of vector magnetometers arranged in a network, comprising the following steps:
  generation (EMi), by a magnetic field source (S), of m reference magnetic fields with known amplitudes and known and distinct directions;
  measurement (MESj) of the m reference magnetic fields along n axes of magnetometers in the network, m and n being such that $m*n \geq 6$;
  determination (LOCj) of the position and orientation of magnetometers of the network from said measurements, relative to the magnetic field source.

The invention also includes a magnetic field measurement instrument that includes a network of vector magnetometers and is capable of implementing the localisation method.

(Continued)

Application to the imagery of biomagnetic fields, for example in magnetocardiography or in magnetoencephalography.

12 Claims, 2 Drawing Sheets

(52) U.S. Cl.
CPC ............ *A61B 5/245* (2021.01); *A61B 5/7203* (2013.01); *A61B 5/725* (2013.01); *G01R 33/00* (2013.01); *G01R 33/0094* (2013.01); *G01V 3/08* (2013.01)

(56) References Cited

U.S. PATENT DOCUMENTS

| | | | |
|---|---|---|---|
| 2009/0253976 A1* | 10/2009 | Harlev | A61B 5/0538 606/41 |
| 2012/0062221 A1* | 3/2012 | Le Prado | G01C 25/005 324/244 |
| 2013/0249784 A1* | 9/2013 | Gustafson | G06F 3/038 345/156 |
| 2016/0084925 A1* | 3/2016 | Le Prado | A61B 5/245 324/301 |

OTHER PUBLICATIONS

U.S. Appl. No. 15/204,230, filed Jul. 7, 2016, 2017/0010337 A1, Sophie Morales et al.*
U.S. Appl. No. 14/809,719, filed Jul. 27, 2015, 2016/0051162 A1, Pierre Durand et al.*
U.S. Appl. No. 14/810,974, filed Jul. 28, 2015, 2016/0051161 A1, Etienne Labyt et al.*
Moving average by Wikipedia, pub. online on Dec. 9, 2016 at <https://en.wikipedia.org/w/index.php?title=Moving_average&oldid=753845041> (Year: 2016).*
French Preliminary Search Report issued Sep. 11, 2017 in French Application 17 50010, filed on Jan. 2, 2017 (with English Translation of Categories of Cited Documents).

* cited by examiner

VECTOR MAGNETOMETERS NETWORK AND ASSOCIATED POSITIONING METHOD

TECHNICAL DOMAIN

The domain of the invention is imagery of biomagnetic fields, and more particularly it concerns networks of vector magnetometers used particularly in magnetocardiography or in magnetoencephalography.

STATE OF PRIOR ART

Magnetoencephalographs used at the present time make use of magnetometers using the SQUID ("Superconducting Quantum Interference Device") technology that are included in a rigid Dewar type support that also contains cryogenic liquids. The disadvantage of these devices is that their invariable geometry is designed to hold the largest heads. Therefore magnetometers distributed particularly around the sides of a magnetoencephalograph helmet are at some distance from the brain of persons with small heads, and particularly children. The result is limited performances.

Networks of vector magnetometers, particularly optical pumping magnetometers, do not require cryogenics, and therefore can be used to design magnetoencephalographs supported by a conformable structure, i.e. with variable geometry, capable of adapting to different patient morphologies (in this case head sizes).

But if the data collected by such a network of magnetometers is to be interpreted correctly, it must be possible to have prior knowledge of the location (position and orientation) of the magnetometers depending on the geometry to be adopted by the conformable support to fit the patient.

PRESENTATION OF THE INVENTION

The invention aims to satisfy this need and discloses a positioning method for at least one vector magnetometer, particularly a magnetocardiography or magnetoencephalography instrument. This method comprises the following steps:
generation of m reference magnetic fields by a magnetic field source, where m is an integer greater than or equal to 2, the amplitudes of the m magnetic fields being known and the directions of the m magnetic fields being known and distinct;
measurement of the m reference magnetic fields along n axes of the at least one vector magnetometer, where n is an integer greater than or equal to 2 and m and n are such that m*n≥6;
determination of the position and orientation of the at least one vector magnetometer relative to the magnetic field source, starting from the measurement of the m reference magnetic fields on the n axes of the at least one vector magnetometer.

Some preferred but non-limitative aspects of this method are as follows:
the m reference magnetic fields are emitted simultaneously, the amplitudes of the m magnetic fields being distinct;
the m reference magnetic fields are emitted sequentially;
the generation step includes a time step in which a reference magnetic field is not generated, and during which a measurement of the ambient magnetic field along the n axes of the at least one vector magnetometer to be localised is made, and the determination step includes subtraction of the measured ambient magnetic field from the m reference magnetic fields;
the magnetic field source makes a frequency modulation of the m reference magnetic fields;
the magnetic field source makes a frequency multiplexing of the m reference magnetic fields;
the magnetic field source comprises m coils and a frequency generator to inject a current with known amplitude into each of the m coils;
the at least one vector magnetometer to be localised belongs to a network of vector magnetometers, and the magnetic field source is a source external to said network;
the at least one vector magnetometer to be localised belongs to a network of vector magnetometers, and the magnetic field source is one of the vector magnetometers in said network;
the generation, measurement and determination steps are reiterated using another vector magnetometer of said network for the magnetic field source;
the measurement and determination steps are implemented by the magnetometer(s) in the network located in an emission zone around the magnetic field source, and said other magnetometer is chosen from among said magnetometer(s) in the network located in the emission zone around the magnetic field source;
the at least one vector magnetometer is carried by a conformable structure and the method includes a prior step to install the conformable structure on a user.

The invention extends to a measurement instrument configured to implement this method.

BRIEF DESCRIPTION OF THE DRAWINGS

Other aspects, purposes, advantages and characteristics of the invention will be better understood after reading the detailed description given below of preferred embodiments of the invention, given as non-limitative examples, with reference to the appended drawings on which.

DETAILED PRESENTATION OF PARTICULAR EMBODIMENTS

Figure 1:
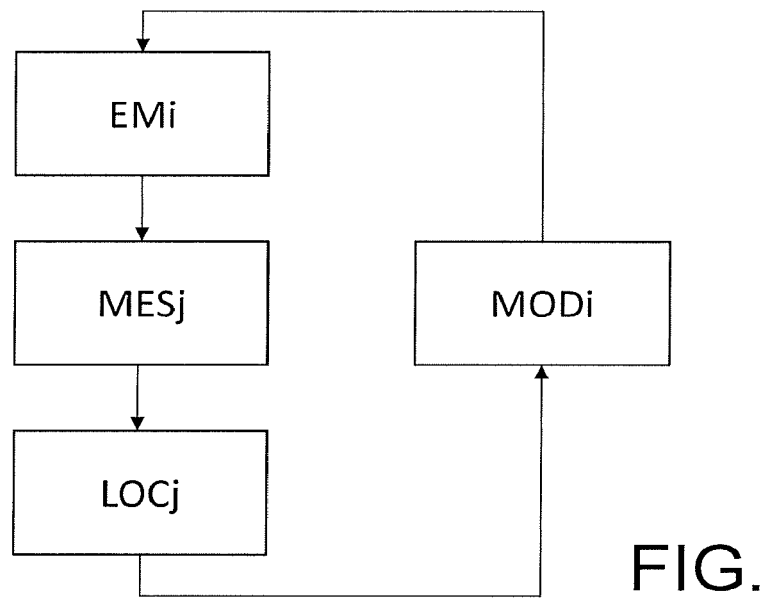
FIG. 1 is a diagram of a possible embodiment of the method according to the invention.

The invention applies to a magnetic field measurement instrument, particularly an instrument that can be applied in the medical field for imagery of biomagnetic fields such as a magnetoencephalograph or a magnetocardiograph and more particularly an instrument comprising vector magnetometers set out in a network. The invention is more particularly applicable to an instrument configured to enable use of the magnetometer localisation method described below.

The network of vector magnetometers is typically carried by a conformable structure that is to be worn by a user, adapted to his morphology. In magnetoencephalography, the conformable structure is in the form of a helmet capable of matching the shape of the head of the user on which it is installed, each magnetometer being in direct contact with the skull.

The method according to the invention thus comprises a prior step to install the conformable structure on the user.

The localisation of the different magnetometers thus depends on the user's morphology, and therefore it is important to be familiar with this localisation before using the instrument for imagery of biomagnetic fields.

The vector magnetometers of the network can be used to measure the magnetic field along a physical direction. For example, they may be optical pumping magnetometers. These magnetometers use a cell filled with a gas of atoms, a laser source that emits a polarised beam towards the cell, and a light detector capable of delivering an output signal representative of the beam that passed through the cell, at least one coil and typically three coils surround the cell and is (are) powered by a frequency generator to generate a sinusoidal magnetic excitation field perpendicular to the polarisation direction of the photons output from the laser if they are linearly polarised and perpendicular to the laser beam if they circularly polarised. The light detector can measure the amplitude of the output signal at a harmonic of the oscillation frequency of the magnetic excitation field. This amplitude is directly proportional to the field to be measured, at least when it is sufficiently weak which is the case for the target applications for which the amplitude of the biomagnetic signals output from the heart or the brain is weaker than 1 nT.

These coils can be used to generate magnetic fields with known amplitudes and directions, in other words with a known magnetic moment $\vec{m}$. In a perfect case, a coil generates a dipolar magnetic field $\vec{B}$ and this dipolar magnetic field with magnetic moment $\vec{m}$ measured at a relative position $\vec{r}$ has the value:

$$\vec{B} = \frac{\mu_0}{4\pi d^5}(3(\vec{m}\cdot\vec{r})\vec{r} - d^2\vec{m}),$$

in which $\mu_0$ is the magnetic permeability of a vacuum and d is the distance between the coil and the relative position. It will be noted that a more advanced measurement of the field $\vec{B}$ at the relative position $\vec{r}$ can be developed from the Biot and Savart equations.

The invention makes use of this possibility to determine the position and the relative orientation of the different magnetometers in the network. It uses one of the magnetometers in the network as the reference magnetic field emitter (a source external to the network can be used as a variant) while the other magnetometers measure the emitted magnetic field. An attempt is then made to determine the position and orientation of the measurement magnetometers relative to the magnetometer that emitted the reference magnetic field.

With reference to FIG. 1, the invention thus applies to a method of localising at least one vector magnetometer that includes the following steps.

A first step includes the generation of m reference magnetic fields by a magnetic field source, where m is an integer greater than or equal to 2, the amplitudes of the m magnetic fields being known and the directions of the m magnetic fields being known and distinct.

A second step includes measurement of the m reference magnetic fields along n axes of at least one vector magnetometer to be localised, where n is an integer greater than or equal to 2 and m and n are such that m*n≥6.

A third step includes the determination of the position and orientation of the at least one vector magnetometer relative to the magnetic field source, starting from the measurement of the m reference magnetic fields on the n axes of the at least one vector magnetometer.

Note that at least 6 uncorrelated measurements are necessary to determine the position and orientation of the magnetometers relative to the magnetic field source. To achieve this, the source generates m≥2 magnetic fields for which the equivalent magnetic moments are directed along distinct directions, these fields being measured on several, n≥2, axes of each magnetometer such that m×n is equal to at least 6. A larger number of measurements provide redundancy, provide more information and filter measurement noise.

The invention thus exploits a magnetic field source that can generate magnetic fields described in a local coordinate system tied to the source, and more particularly a magnetic field source that includes m coils and a frequency generator to inject a current with known amplitude into each of the m coils. Typically, a triaxial source is used that emits three magnetic fields, either simultaneously or sequentially.

The magnetometer(s) to be localised are entities capable of measuring one or several components of a magnetic field. Typically, a triaxial magnetometer measures the projection of the magnetic field vector on three axes described in a coordinate system local to the magnetometer.

Let $\vec{x}_j^i$ be the state vector to be estimated describing the position and orientation of the magnetometer index j to be localised in the coordinate system of the source index i. This vector can for example be composed of 6 or 7 parameters:

3 cartesian coordinates (or another form of coordinates such as cylindrical, spherical, etc.) defining the position of the magnetometer to be localised relative to the source;

3 rotation angles or another equivalent form describing a rotation (for example 3 coordinates of the axis of revolution+angle of rotation, or a quaternion, etc.).

Let $\vec{B}_j^i = \vec{h}(\vec{x}_j^i)$ be the equation describing the measurement of the reference magnetic field(s) emitted by the source i and measured by the magnetometer j. During the localisation step LOCj, the function $\vec{h}(\vec{x}_j^i)$ is inverted to estimate the state vector $\vec{x}_j^i$ from measurements $\vec{B}_j^i$.

In one possible embodiment, the at least one vector magnetometer to be localised belongs to a network of vector magnetometers, and the magnetic field source is a source external to said network. In particular, this source comprises at least m coils surrounding the network and a frequency generator to inject a current with known amplitude into the m coils.

In a second embodiment of the invention, the at least one vector magnetometer to be localised belongs to a network of vector magnetometers, and the magnetic field source is one of the magnetometers in the network. In this second embodiment, the m coils already present on the magnetometers are used to operate one of them as the magnetic field source and a frequency generator to inject a current with known amplitude into each of these m coils.

Optical pumping magnetometers effectively use coils to generate low frequency magnetic fields, for example in the [0-300] Hz range. For example, they are fitted with 1 cm diameter Helmholtz coils, in which each turn is composed of a single wire through which a 1 mA current i passes. Their magnetic moment $\vec{M}_0 = 2.S.i$ $\vec{U}_z = 1.57\times 10^{-7}$ A·m² along the $\vec{U}_z$ axis. This current generates magnetic fields with an amplitude equal to or greater than 2 nT and 2 pT at 2 and 20 cm respectively, that are easily detectable by optical pumping magnetometers that are affected by 200 fT/√Hz noise from 1 to 100 Hz. In the target applications, the magnetometers to be localised are placed at 20 cm from the source magnetometer. All magnetometers in the network can thus detect the magnetic field generated by the source and can be localised.

In this framework, it will be noted that the layout of the magnetometers in the network enable localisation in which the effects of disturbances, mostly with low frequency origin, can be minimised by using a band higher than 10 Hz to avoid the ambient field and lower than 100 Hz to limit Foucault fields. These magnetometers can also emit very low intensity magnetic fields improving the possibility of sequential localisation of magnetometers as described below.

Figure 2:
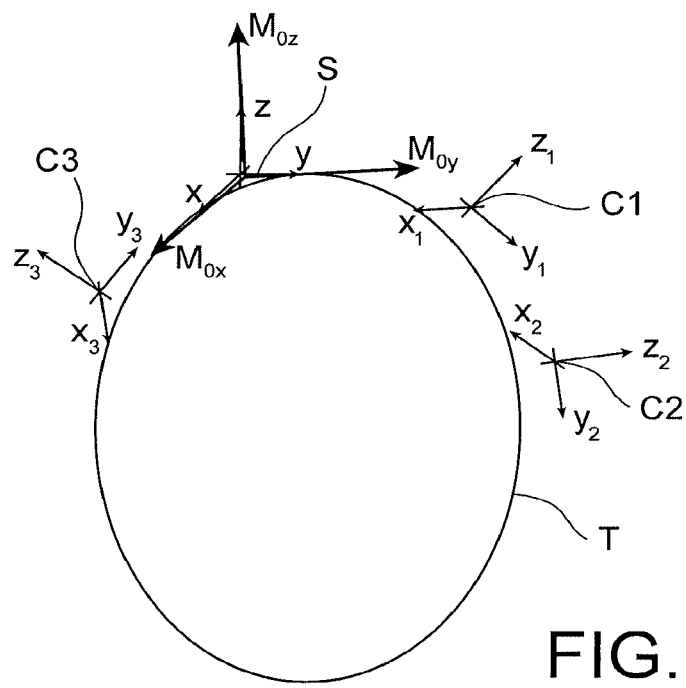
FIG. 2 is a diagram illustrating the localisation of receiver magnetometers relative to an emitter magnetometer.

FIG. 2 illustrates the localisation of receiver magnetometers C1-C3 relative to an emitter magnetometer S, these different magnetometers C1-C3, S forming part of a network of magnetometers fitted on a conformable helmet installed on a user's head T. The emission magnetometer S is controlled to emit a reference magnetic field with known magnetic moment, with amplitude $M_{ox}$, $M_{oy}$, $M_{oz}$ on each of the axes x, y and z of the coordinate system associated with the emission magnetometer S. The method according to the invention can determine the position and orientation of the magnetometers to be localised C1-C3, relative to the emission magnetometer S.

During the step EMi to generate the m reference magnetic fields with known magnetic moments directed along distinct directions, these m fields can be generated sequentially. These fields are thus generated in turn and individually. Since each field is generated continuously in a fixed time interval dedicated to it, we can talk about temporal multiplexing.

The environment of the measurement instrument can be shielded, so as to eliminate the ambient field. As a variant, the environment of the measurement instrument may be not shielded and the temporal multiplexing then includes a time slot in which there is no reference magnetic field generated. The measurement of the ambient magnetic field along the n axes of a vector magnetometer to be localised is then made during said time slot, and determination of the position and orientation of the vector magnetometer relative to the magnetic field source, includes subtraction of the measurement of the ambient magnetic field from the measurement of the reference magnetic fields.

The generated fields are not necessarily continuous, the invention including the generation of variable reference magnetic fields, for example using a frequency modulation of reference magnetic fields introduced by the magnetic field source. The amplitude and phase of the signal received by a magnetometer to be localised can be used to determine the equivalent magnetic field vector. This technique can thus eliminate the ambient field without the need for shielding. In this framework the reference magnetic fields can be generated sequentially, as described above. Alternatively, the magnetic field source uses frequency multiplexing of the m reference magnetic fields that are generated simultaneously, making use of different carrier frequencies on each of the m axes.

The m reference magnetic fields can also be generated simultaneously by making an amplitude modulation of said fields so that the amplitudes of the m magnetic fields are distinct.

Furthermore, the direction of a reference magnetic field is not necessary continuous. This direction can thus be varied, for example to find the direction that maximises the amplitude of the field measured by a magnetometer to be localised.

In the framework of the second embodiment of the invention in which one of the magnetometers in the network is used as the magnetic field source, the generation, measurement and determination steps can be reiterated using another vector magnetometer in said network as the magnetic field source. Thus, several magnetometers in the network can be used in turn to generate the reference fields. This reiteration is illustrated on FIG. 1 by block "MODi" that represents the change in the magnetometer to be used as the reference field source during step EMi.

In the framework of this variant, and after a given number of reiterations, for example equal to the number of magnetometers forming the network such that each has been used in turn as the reference field source, the method can include a step consisting of averaging the positions and orientations of a magnetometer to be localised as determined following the determination steps, so as to obtain a better estimate of the location of the vector magnetometer.

The link between the position of a magnetometer j in a coordinate system i and its position in a reference coordinate system b can be described as follows:

$$\vec{p}_j^i = R_i^b \vec{p}_j^b + \vec{p}_i^b.$$

In this case $\vec{p}_j^i$ is the localisation vector of magnetometer j in the coordinate system of source i and $R_i^b$ is the rotation matrix that describes the orientation of coordinate system i described in coordinate system b. Thus, the localisation vectors $\vec{p}_j^i$ of magnetometer j obtained by making use of different sources i are averaged, expressing these different localisations in the same coordinate system b.

It is possible to find an estimate $\widehat{\vec{p}_i^b}$ of vector $\vec{p}_i^b$ and an estimate $\widehat{R_i^b}$ of matrix $R_i^b$ that minimise the root squares error:

$$(\widehat{R_i^b}, \widehat{\vec{p}_i^b}) = \underset{R_i^b, \vec{p}_i^b}{\operatorname{argmin}} \begin{pmatrix} \vec{p}_1^i - R_i^b \vec{p}_1^b + \vec{p}_i^b \\ \vdots \\ \vec{p}_N^i - R_i^b \vec{p}_k^b + \vec{p}_i^b \end{pmatrix}^T \begin{pmatrix} \vec{p}_1^i - R_i^b \vec{p}_1^b + \vec{p}_i^b \\ \vdots \\ \vec{p}_N^i - R_i^b \vec{p}_N^b + \vec{p}_i^b \end{pmatrix}$$

Euler angles ($\widehat{\vec{\theta}_i^b}$) or the quaternion $\vec{q}_i^b$ that represents the matrix $R_i^b$ can also be found:

$$(\widehat{\vec{\theta}_i^b}, \widehat{\vec{p}_i^b}) = \underset{\vec{\theta}_i^b, \vec{p}_i^b}{\operatorname{argmin}} \begin{pmatrix} \vec{p}_1^i - R(\vec{\theta}_i^b)\vec{p}_1^b + \vec{p}_i^b \\ \vdots \\ \vec{p}_N^i - R(\vec{\theta}_i^b)\vec{p}_N^b + \vec{p}_i^b \end{pmatrix}^T \begin{pmatrix} \vec{p}_1^i - R(\vec{\theta}_i^b)\vec{p}_1^b + \vec{p}_i^b \\ \vdots \\ \vec{p}_k^i - R(\vec{\theta}_i^b)\vec{p}_N^b + \vec{p}_i^b \end{pmatrix}$$

$$(\widehat{\vec{q}_i^b}, \widehat{\vec{p}_i^b}) = \underset{\vec{q}_i^b, \vec{p}_i^b}{\operatorname{argmin}} \begin{pmatrix} \vec{p}_1^i - R(\vec{q}_i^b)\vec{p}_1^b + \vec{p}_i^b \\ \vdots \\ \vec{p}_N^i - R(\vec{q}_i^b)\vec{p}_N^b + \vec{p}_i^b \end{pmatrix}^T \begin{pmatrix} \vec{p}_1^i - R(\vec{q}_i^b)\vec{p}_1^b + \vec{p}_i^b \\ \vdots \\ \vec{p}_k^i - R(\vec{q}_i^b)\vec{p}_N^b + \vec{p}_i^b \end{pmatrix}$$

Weighting can also be added to this minimisation to give more weight to magnetometers that give more precise estimates. The precision of the estimate depends on the signal-to-noise ratio measured by a magnetometer, the receiver magnetometers closest to the transmitter magnetometer being better located than receiver magnetometers at a greater distance. This is done using the weighting matrix mentioned below:

$$(\widehat{\vec{q}_i^b}, \widehat{\vec{p}_i^b}) = \underset{\vec{q}_i^b, \vec{p}_i^b}{\text{argmin}} \begin{pmatrix} \vec{p}_1^i - R(\vec{q}_i^b)\vec{p}_1^b + \vec{p}_i^b \\ \vdots \\ \vec{p}_N^i - R(\vec{q}_i^b)\vec{p}_N^b + \vec{p}_i^b \end{pmatrix}^T W \begin{pmatrix} \vec{p}_1^i - R(\vec{q}_i^b)\vec{p}_1^b + \vec{p}_i^b \\ \vdots \\ \vec{p}_k^i - R(\vec{q}_i^b)\vec{p}_N^b + \vec{p}_i^b \end{pmatrix}$$

Always in the second embodiment in which one of the magnetometers in the network is used as a magnetic field source, the measurement and determination steps may be implemented by the magnetometer(s) in the network located in a predetermined emission zone around the magnetic field source. The emission zone typically covers magnetometers closest to the source magnetometer, for example magnetometers close to a given maximum of hops of the reference magnetometer in the network (a single-hop magnetometer corresponding to an immediately adjacent magnetometer). It is then possible to reiterate the different steps in the method by using a magnetometer present in the emission area around the magnetometer used as source in the previous iteration, as the new source magnetometer.

It can be arranged to have a sequential localisation that guarantees good precision of the estimate, that effectively depends on the signal-to-noise ratio such that the closest magnetometers are better localised that magnetometers at a larger distance. This sequential localisation enables incremental step by step localisation. The position of all the magnetometers can be determined sequentially in the coordinate system of one of the emitting magnetometers according to $\vec{p}_j^i = R_i^b \vec{p}_j^b + \vec{p}_i^b$, in which $R_i^b$ is the rotation matrix of the coordinate system related to source i described in the coordinate system related to source b, and $\vec{p}_i^b$ is the vector describing the position of source i in the coordinate system related to source b. Therefore, the positions of the sensors can be determined sequentially step by step, expressed in the coordinate system related to source b.

In one advantageous variant, the new magnetometer to be used as the source for a new iteration has an emission zone that overlaps with the emission zone of the magnetometer used as the source during a previous iteration.

Figure 3:
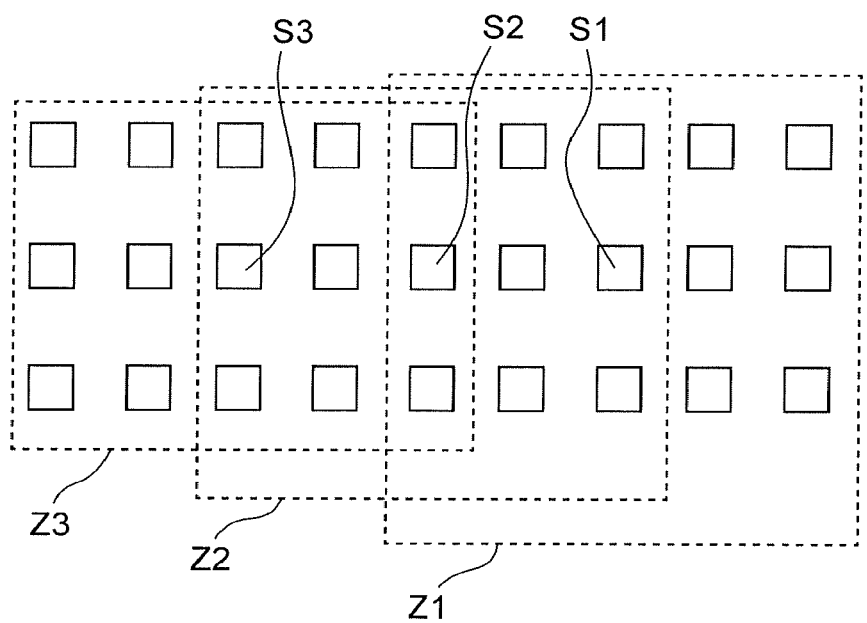
FIG. 3 represents a step by step localisation with overlap, that can be used in the framework of the invention.

FIG. 3 shows an example of a network with successive overlapping emission zones. On this figure, during a first iteration of the method, a first magnetometer S1 is used as source with a first emission zone Z1. A second magnetometer S2 is found in this first emission zone Z1, and its localisation relative to the first magnetometer S1 are found. During a second iteration of the method, the second magnetometer S2 is used as source with a second emission zone Z2. The first magnetometer S1 and a third magnetometer S3 are found in this second emission zone Z2, and their localisations relative to the second magnetometer S2 are found. During a third iteration of the method, the third magnetometer S3 is used as source with a third emission zone Z3. The second magnetometer S2 is found in this third emission zone Z3, and its localisation relative to the third magnetometer S3 is found. By allowing overlapping emission zones, the localisation of the second magnetometer S2 relative to the first magnetometer S1 and its localisation relative to the third magnetometer S3 are found. It is thus possible to make a better estimate of the localisation of the second magnetometer S2 relative to the different source magnetometers. And as presented above, it is possible to sequentially determine an absolute localisation, for example relative to a single magnetometer index b in the network, of each magnetometer in the network. For example, starting from the localisation of the third magnetometer S3 relative to the second magnetometer S2, and knowing the localisation of the second magnetometer S2 relative to the first magnetometer S1, the localisation of the third magnetometer S3 relative to the first magnetometer S1 can be determined.

These sequential localisations or localisations by overlapping zones provide a means of solving the problem of limited emission power that can be generated by a source magnetometer that can make it impossible to estimate the position due to ambient noise affecting the measurement by a measurement magnetometer. The field can also be reduced to zero by shielding the measurement instrument to eliminate this ambient noise.

The invention is not limited to the method as described above, but also includes a magnetic field measurement instrument such as a magnetocardiograph or magnetoencephalograph apparatus, and particularly an apparatus comprising:

a magnetic field source configured to generate m reference magnetic fields, where m is an integer greater than or equal to 2, the amplitudes of the m magnetic fields being known and the directions of the m magnetic fields being known and distinct;

at least one vector magnetometer configured to measure the m reference magnetic fields along n axes, where n is an integer greater than or equal to 2 and m and n are such that m*n≥6; and a computer configured to determine the position and orientation of the at least one vector magnetometer relative to the magnetic field source, starting from the measurement of the m reference magnetic fields on the n axes of the at least one vector magnetometer.

We have already seen that equation $\vec{B}_j^i = \vec{h}(\vec{x}_j^i)$ describes the measurement of the reference magnetic field(s) emitted by source i and measured by magnetometer j and that function $\vec{h}(\vec{x}_j^i)$ is inverted during the localisation step to estimate the state vector $\vec{x}_j^i$ from measurements $\vec{B}_j^i$.

The solution to this inversion problem is usually not determined precisely due to the presence of noise that confers a probabilistic nature onto the measurements. Therefore an estimator is used to determine the state vector that minimises a clearly defined criterion with an optional evolution model that can be used to monitor the position of the magnetometers in time. Therefore the concept of time is introduced that can subsequently add filtering to the measurements:

$$\vec{B}_j^i(t) = \vec{h}(\vec{x}_j^i(t)) + \vec{\omega}_j^i(t)$$

In this case, $\vec{\omega}_j^i$ is measurement noise on the field emitted by i and measured by j. It is a random variable that depends on the characteristics of the emitter and the receiver. This noise is often dominated by thermal noise.

A first example of a possible technique for performing this inversion at a time t is a least squares type minimisation. The purpose is to determine the value $\widehat{\vec{x}_j^i}(t)$ that minimises the squared error between the real measurement and the estimated measurement:

$$\widehat{\vec{x}_j^i}(t) = \underset{\vec{x}_j^i(t)}{\text{argmin}} \left( \left[ \vec{h}(\vec{x}_j^i(t)) - \vec{B}_j^i(t) \right]^T \left[ \vec{h}(\vec{x}_j^i(t)) - \vec{B}_j^i(t) \right] \right)$$

Since this function is not linear, optimisation techniques such as the gradient descent, Gauss-Newton or Levenberg-Marquardt can be used.

In the special case in which the constellation of fixed or quasi-fixed magnetometer positions is being estimated, it can be assumed that the position $\widehat{\vec{x}}_j^i(t)$ does not vary in a time window of n samples. This makes it possible to improve filtering of sensor noise by averaging information obtained by measurements at time $t_i$. The function to be minimised then becomes:

$$\widehat{\vec{x}}_j^i = \underset{\vec{x}_j^i}{\operatorname{argmin}} \left( \left[ \begin{bmatrix} \vec{h}(\vec{x}_j^i(t_1)) \\ \vdots \\ \vec{h}(\vec{x}_j^i(t_n)) \end{bmatrix} - \begin{bmatrix} \vec{B}_j^i(t_1) \\ \vdots \\ \vec{B}_j^i(t_n) \end{bmatrix} \right]^T \left[ \begin{bmatrix} \vec{h}(\vec{x}_j^i(t_1)) \\ \vdots \\ \vec{h}(\vec{x}_j^i(t_n)) \end{bmatrix} - \begin{bmatrix} \vec{B}_j^i(t_1) \\ \vdots \\ \vec{B}_j^i(t_n) \end{bmatrix} \right] \right)$$

According to a second example of the inversion technique, a maximum likelihood estimator is used to find $\widehat{\vec{x}}_j^i(t)$ that maximises the probability of obtaining real measurements (i.e. the $\vec{B}_j^i$)

$$\widehat{\vec{x}_j^i(t)} = \underset{\vec{x}_j^i(t)}{\operatorname{argmax}} \, l\!\left(\vec{x}_j^i(t), \vec{B}_j^i(t)\right)$$

In this case, l is the Likelihood function.

As for the previous case, it can be assumed that the position $\widehat{\vec{x}}_j^i(t)$ does not vary in a time window of n samples. The estimator then becomes:

$$\widehat{\vec{x}}_j^i = \underset{\vec{x}_j^i}{\operatorname{argmax}} \, l\!\left(\vec{x}_j^i, \vec{B}_j^i(t_1), \ldots, \vec{B}_j^i(t_n)\right)$$

A probabilistic framework is used in this technique. It is therefore possible to introduce physical information about the quality of the measurement given by the magnetometers.

In another example of an inversion technique, an evolution model is used to filter measurements in time and to make it possible for magnetometers to move in time. Algorithms suitable for use in this framework are often Bayesian estimating algorithms such as Kalman filters or particle filters.

For example, using a discrete form of a Kalman filter and using the identity as an evolution function (it is assumed that the sensor can move at random (Gaussian) around its position at the previous time), the starting point is the following state system:

$$\vec{x}_j^i(t_k) = \vec{x}_j^i(t_{k-1}) + \vartheta_j^i(t_{k-1})$$

$$\vec{B}_j^i(t_k) = \vec{h}(\vec{x}_j^i(t_k)) + \omega_j^i(t_k)$$

In this case $\vartheta_j^i(t_{k-1})$ is the state noise that describes the uncertainty on the magnetometer movement between time $t_{k-1}$ and time $t_k$ (it is assumed that it is Gaussian noise centred on the covariance matrix $Q_j^i(t_{k-1})$). $\omega_j^i(t_k)$ is the measurement noise that describes noise that modifies the measurement (it is assumed that it is Gaussian noise centred on the covariance matrix $R_j^i(t_k)$).

The Kalman filter optimally estimates (if the function is linear and noise is Gaussian) the state vector $\vec{x}_j^i(t_k)$ at each instant $t_k$ while filtering this estimate using information accumulated from the past and probabilities describing the variation of the state with time. The Kalman filter processes the state vector as a Gaussian random vector described by an expectancy $\widehat{\vec{x}}_j^i(t_k)$ and a covariance matrix $\widehat{P}_j^i(t_k)$.

An initial estimate of the state is necessary. This is a random variable because the positions of the magnetometers at the beginning of the experiment are not known very precisely. This initialisation is a priori knowledge of the positions of the magnetometers. It is described by an expectancy $\widehat{\vec{x}}_j^i(t_0)$ and a covariance matrix $\widehat{P}_j^i(t_0)$ that provides information about uncertainty on this initial position.

At each measurement instant $t_k$, the magnetometers measure magnetic fields emitted by the source and estimate their state in two steps. The first step called prediction, uses the first state equation to estimate the current state as a function of the previous state:

$$\vec{x}_j^i(t_k)^* = \vec{x}_j^i(t_{k-1})$$

$$\widehat{P}_j^i(t_k)^* = \widehat{P}_j^i(t_{k-1}) + Q_j^i(t_{k-1})$$

The second phase of the algorithm consists of updating this estimate using the measurement made at time $t_k$. This correction is made as follows:

$$\vec{x}_j^i(t_k) = \vec{x}_j^i(t_k)^* + K\vec{y}_j^i(t_k)$$

$$\widehat{P}_j^i(t_k) = (I - K_j^i(t_k) H(\vec{x}_j^i(t_k))) \widehat{P}_j^i(t_k)^*$$

In which H is the Jacobean matrix of function $\vec{h}$. $\vec{y}_j^i(t_k)$ is the innovation made by the measurement at time $t_k$:

$$\vec{y}_j^i(t_k) = \vec{B}_j^i(t_k) - \vec{h}(\vec{x}_j^i(t_k))$$

$K_j^i(t_k)$ is the Kalman gain calculated as follows:

$$K_j^i(t_k) = \widehat{P}_j^i(t_k)^* H^T(\vec{x}_j^i(t_k)) S_j^{i^{-1}}(t_k)$$

$S_j^i(t_k)$ is the covariance matrix of the innovation calculated as follows:

$$S_j^i(t_k) = H(\vec{x}_j^i(t_k)) \widehat{P}_j^i(t_k)^* H^T(\vec{x}_j^i(t_k)) + R_j^i(t_k).$$

The invention claimed is:

1. A method for localization of at least one vector magnetometer belonging to a network of vector magnetometers, the network including a first emission zone and an overlapping second emission zone, each emission zone including a number of the vector magnetometers, the method comprising:

controlling, for the first emission zone, a first vector magnetometer to be a source vector magnetometer, the source vector magnetometer being one of the vector magnetometers in the first emission zone but not in the second emission zone, such that the source vector magnetometer generates m reference magnetic fields, where m is an integer greater than or equal to 2, amplitudes of the m magnetic fields being known and directions of the m magnetic fields being known and distinct;

measuring, by a measurement vector magnetometer, the measurement vector magnetometer being a second vector magnetometer, different from the first vector magnetometer, of the vector magnetometers in the first emission zone, the second vector magnetometer being also in the second emission zone and in range of the first vector magnetometer, the m reference magnetic fields along n axes of the measurement vector magnetometer, where n is an integer greater than or equal to 2 and m and n are such that m*n≥6;

determining a position and an orientation of the measurement vector magnetometer relative to the source vector magnetometer, using the measurement of the m reference magnetic fields on the n axes of the measurement vector magnetometer; and repeating the controlling, measuring, and determining steps for the second emission zone by controlling the second vector magnetometer to be the source vector magnetometer, rather than the measurement vector magnetometer, and using a third vector magnetometer, different from the first and second vector magnetometers, as the measurement vector magnetometer, wherein the third vector magnetometer is in the second emission zone, but not in the first emission zone, and is in range of the second vector magnetometer, but is out of range of the first vector magnetometer, so that a localization of the second vector magnetometer is found relative to the first and third vector magnetometers, even though the third vector magnetometer is out of range of the first vector magnetometer.

2. The method according to claim 1, wherein the m reference magnetic fields are emitted simultaneously, and the amplitudes of the m magnetic fields are distinct.

3. The method according to claim 1, wherein the m reference magnetic fields are emitted sequentially.

4. The method according to claim 3, wherein the controlling step includes a time slot in which a reference magnetic field is not generated, and measuring an ambient magnetic field along the n axes of the measurement vector magnetometer during the time slot, and the determining step includes subtracting the measured ambient magnetic field from the measured m reference magnetic fields.

5. The method according to claim 1, in which the source vector magnetometer makes a frequency modulation of the m reference magnetic fields.

6. The method according to claim 5, wherein the source vector magnetometer makes a frequency multiplexing of the m reference magnetic fields.

7. The method according to claim 1, wherein the source vector magnetometer comprises m coils and a frequency generator to inject a current with a known amplitude into each of the m coils.

8. The method according to claim 1, further comprising averaging values of the position and the orientation of the measurement vector magnetometer after repeated performance of the determining step.

9. The method according to claim 1, wherein the measuring and determining steps are implemented by the measurement vector magnetometer, which is located in an emission zone around the source vector magnetometer, and wherein the measurement vector magnetometer is chosen from among the vector magnetometers in the network located in the emission zone around the source vector magnetometer.

10. The method according to claim 1, wherein the measurement vector magnetometer is carried by a conformable structure, and the method includes installing the conformable structure on a user.

11. The method of claim 1, further comprising:
repeating the controlling, measuring, and determining steps by controlling the second vector magnetometer in the network of vector magnetometers, different from the first vector magnetometer, to be the source vector magnetometer and controlling a third vector magnetometer, different from the first and second vector magnetometers, to be the measurement vector magnetometer so as to sequentially determine (1) a first position being a position of the second vector magnetometer relative to the first vector magnetometer, and (2) a second position being a position of the third vector magnetometer with respect to the second vector magnetometer; and determining a position of the third vector magnetometer relative to the first vector magnetometer based on the first and second positions.

12. A magnetic field measurement instrument, comprising:
a network of vector magnetometers, the network including a first emission zone and an overlapping second emission zone, each emission zone including a number of the vector magnetometers, the network including
a first vector magnetometer being controlled, for the first emission zone, to be a source vector magnetometer configured to generate m reference magnetic fields, where m is an integer greater than or equal to 2, amplitudes of the m magnetic fields being known and directions of the m magnetic fields being known and distinct, the first vector magnetometer not being in the second emission zone, and
a second vector magnetometer, different from the first vector magnetometer, serving as a measurement vector magnetometer, for the first emission zone, the second vector magnetometer being also in the second emission zone and in range of the first vector magnetometer and configured to measure m reference magnetic fields along n axes of the measurement vector magnetometer, where n is an integer greater than or equal to 2 and m and n are such that $m*n \geq 6$; and circuitry configured to control, for the first emission zone, the first vector magnetometer to be the source vector magnetometer, and determine a position and an orientation of the measurement vector magnetometer relative to the source vector magnetometer, using the measurement of the m reference magnetic fields on the n axes of the measurement vector magnetometer, wherein the circuitry is further configured to
repeat the controlling and determining steps for the second emission zone by controlling the second vector magnetometer to be the source vector magnetometer, rather than the measurement vector magnetometer, and using a third vector magnetometer, different from the first and second vector magnetometers, as the measurement vector magnetometer, wherein the third vector magnetometer is in the second emission zone, but not in the first emission zone, and is in range of the second vector magnetometer, but is out of range of the first vector magnetometer, so that a localization of the second vector magnetometer is found relative to the first and third vector magnetometers, even though the third vector magnetometer is out of range of the first vector magnetometer.

* * * * *